(12) United States Patent
Chawla (10) Patent No.: US 10,806,440 B2
(45) Date of Patent: Oct. 20, 2020

(54) MITRAL PAPILLARY MUSCLE EXPOSURE DEVICE

(71) Applicant: Surendra K. Chawla, Bloomfield, CT (US)

(72) Inventor: Surendra K. Chawla, Bloomfield, CT (US)

( * ) Notice: Subject to any disclaimer, the term of this patent is extended or adjusted under 35 U.S.C. 154(b) by 0 days.

(21) Appl. No.: 16/538,116

(22) Filed: Aug. 12, 2019

(65) Prior Publication Data

US 2020/0060670 A1 Feb. 27, 2020

Related U.S. Application Data

(60) Provisional application No. 62/722,267, filed on Aug. 24, 2018.

(51) Int. Cl.
*A61B 17/02* (2006.01)
*A61B 1/32* (2006.01)
(Continued)

(52) U.S. Cl.
CPC .......... *A61B 17/0218* (2013.01); *A61B 1/06* (2013.01); *A61B 1/32* (2013.01);
(Continued)

(58) Field of Classification Search
CPC ....... A61B 1/32; A61B 17/02; A61B 17/0206; A61B 17/0218; A61B 2017/0237
See application file for complete search history.

(56) References Cited

U.S. PATENT DOCUMENTS 4,116,232 A * 9/1978 Rabban ................. A61B 17/02 600/196
5,944,736 A * 8/1999 Taylor ............... A61B 17/0206 606/198

(Continued)

FOREIGN PATENT DOCUMENTS

WO 2014/168655 A1 10/2014
WO WO-2017218504 A1 * 12/2017 ......... A61B 17/0218

OTHER PUBLICATIONS

"Collar Papillary Muscle Exposure Device—Brochure", Miami Instruments, 2017, http://www.miamiinstruments.com-about-our-products/exposure-products/collar-papillary-muscle-exposure-device-product-brochure/.

(Continued)

*Primary Examiner* — Larry E Waggle, Jr.
(74) *Attorney, Agent, or Firm* — Lathrop GPM LLP; Wm. Tucker Griffith (57) ABSTRACT

A hands-free mitral papillary muscle exposure device provides a clear view of the papillary muscles, including the pathology of the leaflets and chordae tendineae of a mitral valve apparatus, and comprises a retractor device comprises two arm members pivotally connected to one another which can be manually spread and adjusted about a pivot point to a desired arrangement relative to the mitral valve apparatus to prevent injury to surrounding muscle and tissue during an operative procedure. Each arm member includes a respective downwardly extending longitudinal projection to hold one of the anterior and posterior leaflets adjacent to said arm member when the retractor device is positioned relative to the mitral valve apparatus. The longitudinal projection on the anterior side of the retractor device is longer than the corresponding longitudinal projection on the posterior side (Continued)

to accommodate the longer size of the anterior leaflet in comparison with the posterior leaflet.

26 Claims, 8 Drawing Sheets

(51) Int. Cl.
*A61B 1/06* (2006.01)
*A61B 17/00* (2006.01)

(52) U.S. Cl.
CPC ............... *A61B 2017/00477* (2013.01); *A61B 2017/0237* (2013.01); *A61B 2217/005* (2013.01)

(56) References Cited

U.S. PATENT DOCUMENTS

| | | | | |
|---|---|---|---|---|
| 6,260,552 | B1* | 7/2001 | Mortier | A61B 17/00234 128/898 |
| 6,837,851 | B1* | 1/2005 | Valentini | A61B 17/0206 600/210 |
| 6,852,075 | B1* | 2/2005 | Taylor | A61B 17/00 600/37 |
| 6,997,950 | B2 | 2/2006 | Chawla | |
| 7,338,441 | B2* | 3/2008 | Houser | A61B 17/0218 600/206 |
| 7,922,657 | B2* | 4/2011 | Gillinov | A61B 17/02 600/210 |
| 8,388,525 | B2 | 3/2013 | Poo et al. | |
| 2014/0309727 | A1 | 10/2014 | Lamelas et al. | |

OTHER PUBLICATIONS

Tabata MD, et al., "A Simple, Effective, and Inexpensive Technique for Exposure of Papillary Muscles in Minimally Invasive Mitral Valve Repair: Wakka Technique", The Society of Thoracic Surgeons, 2015; 100:e59-61.

Erlebach, MD, et al., "Placement of Neochords in Mitral Valve Repair: Enhanced Exposure of the Papillary Muscles Using a Standard Valve Sizer", The Society of Thoracic Surgeons, 2016; 101:378-80.

Tudorache, MD, et al., "Enhanced exposure of subvalvular structures during mitral valve repair with a novel flexible and reusable leaflets retractor", The Journal of Thoracic and Cardiovascular Surgery, vol. 156, No. 2 (2018).

Hixenbaugh, Mike, "In Miami, he pioneered new approaches to heart surgery. Now he hopes to do the same in Houston", Houston Chronicle, Mar. 24, 2017, http://www.houstonchronicle.com/local/prognosis/article/In-Miami-he-pioneered-new-approaches-to-heart-11023077/php.

Chawla, MD, Surendra K, et al., "Performance and healing of an expanded polytetrafluoroethylene multichordal device at 6 months after repair of mitral leaflet flail in swine", The Journal of Thoracic and Cardiovascular Surgery, Mar. 2019, vol. 157, No. 3, 940.e3.

Chawla, MD, Surendra K, et al., "Use of a New Expanded Polytetrafluorethylene Muntichordal Mitral Apparatus (MitraPatch) to Repair Complex Mitral Valve Lesions", Innovations, vol. 12, No. 6, Nov./Dec. 2017, pp, 411-417.

Chawla, Surendra, K., et al., "Pre-clinical Experience with a Multi-Chordal Patch for Mitral Valve Repair", J. of Cardiovasc. Trans. Res., Published online: Jan. 22, 2016, DOI 10.1007/s12265-016-9674-4.

\* cited by examiner

MITRAL PAPILLARY MUSCLE EXPOSURE DEVICE

CROSS-REFERENCE TO RELATED APPLICATION

This application claims the benefit under 35 U.S.C. § 119(e) of U.S. Provisional Application No. 62/722,267, filed Aug. 24, 2018, which is hereby incorporated by reference in its entirety.

FIELD OF THE INVENTION

The present invention relates generally to retractor devices for holding tissue during surgery, and more particularly relates to a hands-free mitral papillary muscle retractor device for use during heart surgery for mitral valve repairs.

BACKGROUND OF THE INVENTION

Figure 1A:
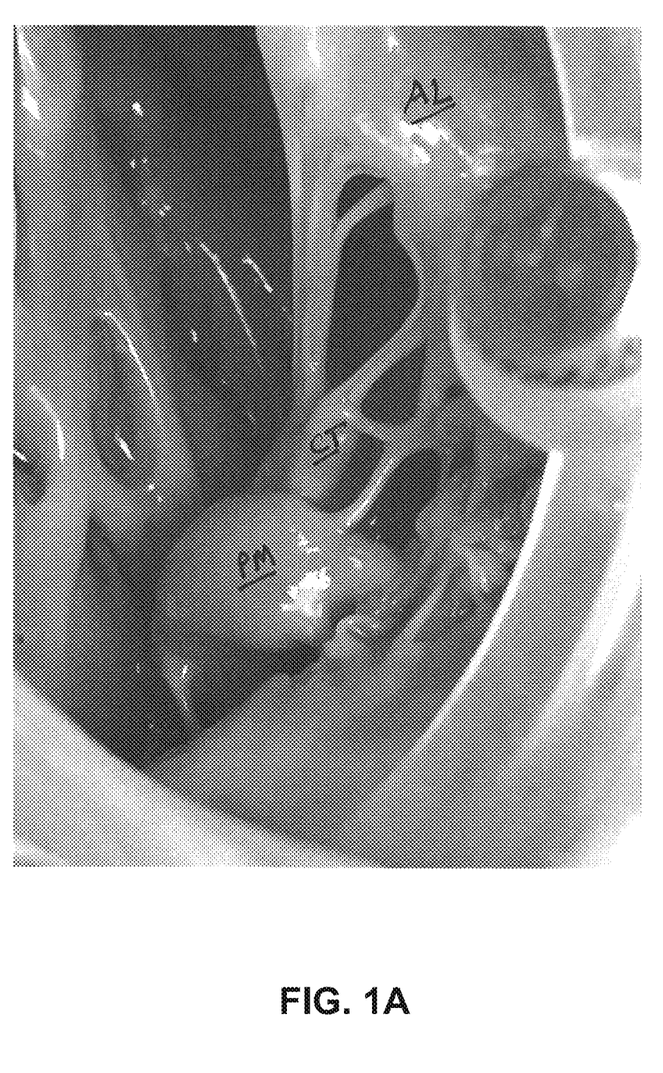
FIG. 1A is an image of a mitral valve apparatus.

The present invention is generally directed to an exposure device, or retractor, capable of exposing the entire mitral valve apparatus during repair of the mitral valve for mitral regurgitation. In the context of the present invention, the "mitral valve apparatus" generally constitutes the mitral leaflets, chordae tendineae, and the papillary muscles, which arises from the heart muscle. The mitral valve apparatus is partially shown in the photograph of FIG. 1A and generally schematically illustrated in FIG. 1B. A simulated intraoperative image of mitral valve exposure is shown in FIG. 2, illustrating the depth of the mitral valve in an operative setting and thus providing some context for the exposure device of the present invention.

The mitral valve MV is located on the left side of the heart between the left atrium and the left ventricle. The left atrium receives oxygenated blood from the four pulmonary veins passing through the mitral valve MV into the left ventricle to be pumped into the entire body through the aortic valve. Prevention of malocclusion of the mitral valve MV is controlled by multiple chordae tendineae CT, which are attached to two papillary muscles PM, the anterolateral papillary muscle and the posteromedial papillary muscle; the posteromedial papillary muscle is shown in FIG. 1A.

Figure 1B:
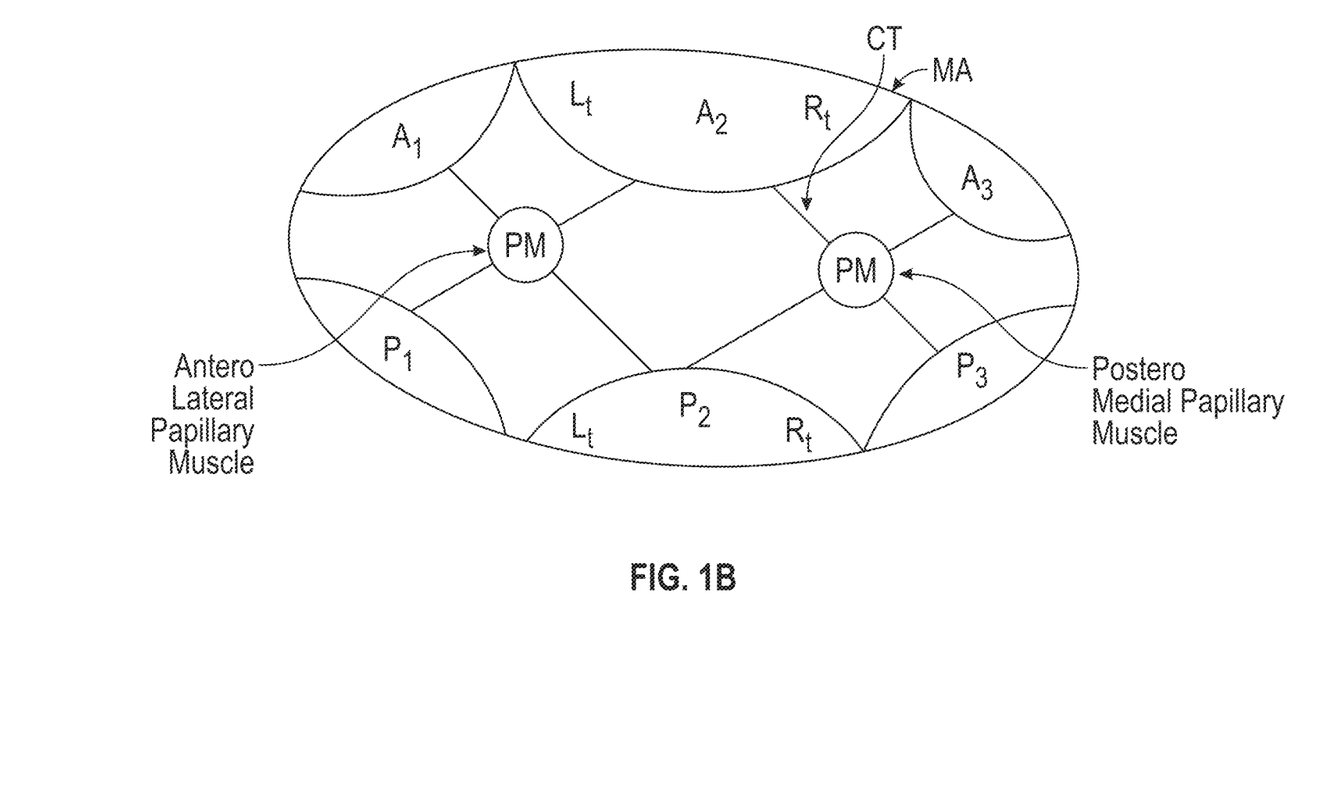
FIG. 1B is a schematic illustration of the mitral valve apparatus of FIG. 1A.
Figure 2:
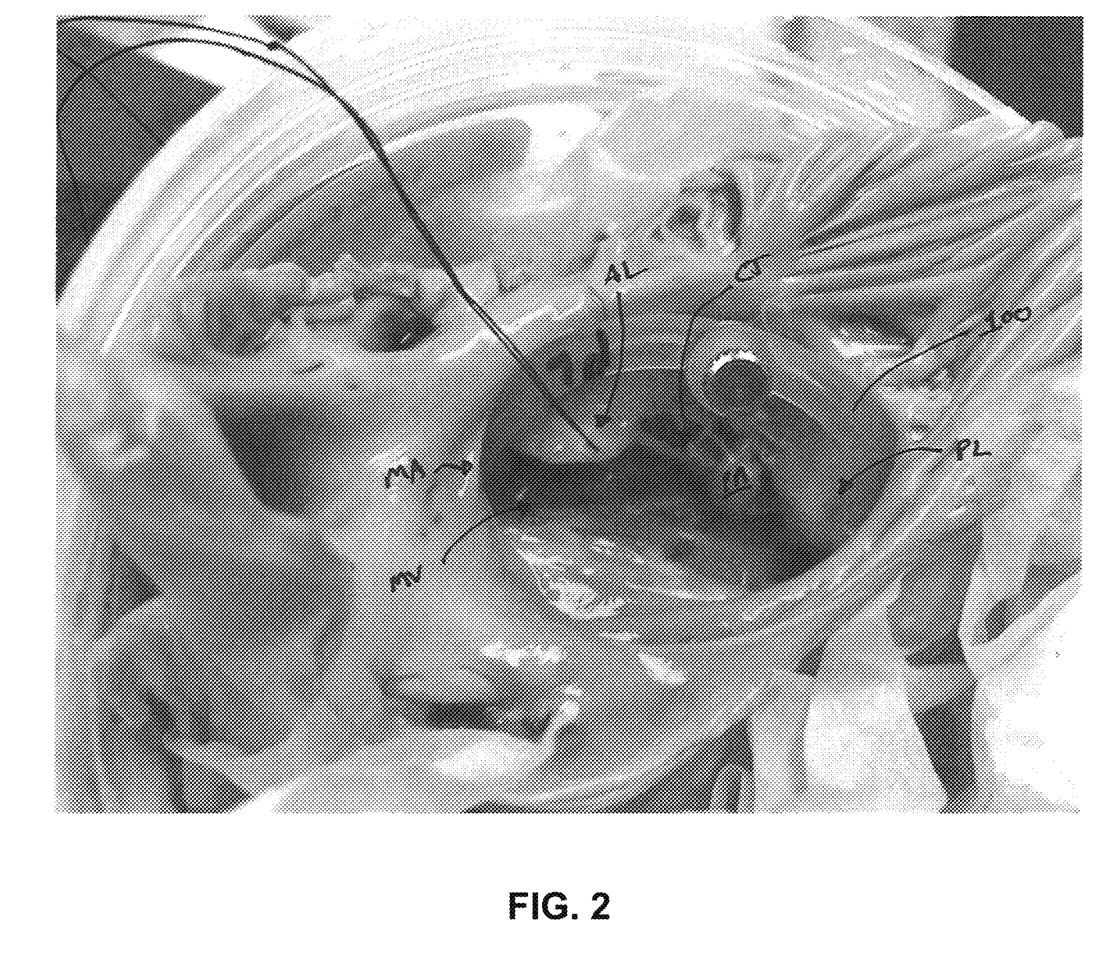
FIG. 2 is a cadaver heart picture of mitral valve exposure using a hands-free mitral papillary muscle retractor device in accordance with the present invention and illustrating the mitral valve cavity and access point thereof during a common operative procedure.

Referring to FIG. 1B, the mitral valve MV consists of two leaflets—the anterior leaflet AL and the posterior leaflet PL. These two leaflets AL, PL open during relaxation of the heart, and close when the heart contracts while pushing blood into the body. During such pumping of the heart, the chordae tendineae CT are pulled tight to keep the leaflet edges approximated, aiding to coapt the two leaflets AL, PL and thereby prevent any blood from returning back into the atrium via the mitral valve MV, also known as regurgitation.

Still referring to FIG. 1B, the anterior leaflet AL generally comprises three sections, designated as A1, A2 and A3. FIG. 1B further generally identifies two separate portions of the middle leaflet A2, which includes a central portion, where there generally are no chordae CT, as illustrated, allowing designation of a left part Lt adjacent to section A1 and generally associated with the anterolateral papillary muscle, and a right part Rt adjacent to section A3 and generally associated with the posteromedial papillary muscle. The posterior leaflet PL similarly comprises three sections, designated as P1, P2 and P3, with the central section being split into a left part Lt and a right part Rt that generally mirror corresponding parts of the anterior leaflet AL.

Myxomatous disease of the mitral valve MV can lead to elongation of the chordae tendineae CT causing prolapse or rupture, which, in turn, causes flail of a segment of the leaflet AL and/or PL, which, in turn, may lead to mitral regurgitation, dilation of the heart, heart failure, and even death. The standard and preferable treatment for myxomatous disease is mitral valve repair rather than replacement. Mitral valve repair allows for preservation of the patient's own tissues, avoiding anticoagulation and having low operative mortality. Clinical observation has generally indicated that the majority of the pathological flail (tear) occurs in chordae tendineae CT originating at leaflets A2 and/or P2. Thus, mitral valve repair is generally needed for these sections of the anterior and posterior leaflets AL and PL.

Mitral valve repair is generally performed by quadrangular or triangular resection, sliding plasty or using ePTFE (Goretex) sutures/loops for the posterior leaflet PL and mostly preferred ePTFE sutures for the anterior leaflet AL. During GoreTex suture repair procedures, the sutures are passed through the papillary muscles PM and then passed through the leaflet at the site of elongation or rupture, and tied at the appropriate level to achieve good cooptation, preventing regurgitation. Devices used for mitral valve repair include Applicant's own MitraPatch inventions, described and shown in U.S. Pat. Nos. 6,997,950 and 9,248,018, each incorporated herein by reference.

Heretofore, the exposure of the papillary muscles PM has been challenging. To expose the papillary muscle PM, the surgeon needs to retract the leaflets AL, PL. Prior art devices exist that aid in retracting and holding the tissue to expose the mitral valve apparatus, and generally include rigid plastic materials that can be flexed into position to hold back the leaflets AL, PL and tissue relative to the mitral valve apparatus. However, such devices are often difficult to position or adjust once in position; do not adequately hold the muscle and tissue; and can easily damage the muscle, tissue and mitral valve apparatus if mispositioned or adjusted. Indeed, such devices generally rely upon the rigidity of the material to hold muscle and tissue back, but such rigidity and biasing forces actual make it difficult to use such devices, and as a result, such devices are generally difficult to manually adjust to account for particular patients' pathology once in position.

For example, the commercially available COLLAR™ device, from Miami Instruments LLC, is constructed from a rigid plastic, and can be flexed into a compressed state to insert into position. Once in position, the device can be relaxed to take form in the mitral valve cavity. However, once the COLLAR™ device is positioned, it typically requires extra manipulation to adjust or change position or orientation. Such manipulation can risk damage to the mitral valve apparatus. Similar constructions are available, such as the Wakka technique by Minoru Tabata, which uses a sterile surgical marker and attached paper ruler, as described in Minoru Tabata, M D, M P H, et al., "A Simple, Effective, and Inexpensive Technique for Exposure of Papillary Muscles in Minimally Invasive Mitral Valve Repair: Wakka Technique," Ann. Thorac. Surg., 2015, 100:e59-61; a standard valve sizer introduced by Magdalena Erlebach, M D et al., "Placement of Neochords in Mitral Valve Repair: Enhanced Exposure of the Papillary Muscles Using a Standard Valve Sizer," Ann. Thorac. Surg., 2016, 101:378-380; and a recent device comprising a rolled-up flat retractor, and described in Igor Tudorache, M D et al., "Enhanced exposure of subvalvular structures during mitral valve repair with a novel flexible and reusable leaflets retractor," I. Thorac. Cardiovasc. Surg., 2018, 156:643-645. Each of these prior art devices and approaches uses the common feature of providing a tunnel vision of the two papillary muscles PM and covering the rest of the mitral apparatus, including the anterior and posterior leaflets AL and PL and part of the chordae tendineae CT. Little control for positioning the devices is provided. Moreover, once positioned, the devices are difficult to adjust and safely remove. Additionally, the anterior leaflets AL are generally longer than the posterior leaflets PL. Thus, devices that do not accommodate such structural differences between the anterior and posterior leaflets AL and PL, or even appreciate the distinctions between the anterior lateral and posterior medial sides of the mitral valve apparatus are less than optimal solutions.

Accordingly, it is the general aim of the present invention to provide an improved, mitral valve apparatus exposure device that includes a hands-free mitral papillary muscle retractor that is easy to position, adjust and use during surgery relative to the mitral valve that overcomes the problems and drawbacks associated with prior art retractor devices, and therefore significantly improves the utility of such retractor devices during mitral valve surgical procedures.

SUMMARY OF THE INVENTION

In accordance with embodiments of the present invention, a hands-free mitral papillary muscle exposure device comprises a retractor device that provides a clear view of the pathology of the leaflets and chordae tendineae of a mitral valve apparatus, while also providing a clear view of the entire papillary muscle needing repair. Such a retractor device comprises two arm members pivotally connected to one another which can be manually spread and adjusted about a pivot point to a desired arrangement relative to the mitral valve apparatus to prevent injury to surrounding muscle and tissue during an operative procedure. Each arm member includes a respective downwardly extending longitudinal projection to hold one of the anterior and posterior leaflets adjacent to said arm member when the retractor device is positioned relative to the mitral valve apparatus.

In use, the retractor device is generally placed at the opening or rim (i.e., the mitral annulus MA) of the mitral valve cavity. The longitudinal projections project into the mitral valve cavity. The retractor device is inserted into the body in a relaxed condition—that is, with the arm members generally pivoted together—and once at the opening and rim MA to the mitral valve cavity, the arm members can be pivoted outwardly and away from one another about the pivot point, pushing back the anterior and posterior leaflets AL, PL and chordae tendineae CT until the separation and shape of the arm members generally correspond to the shape of the mitral annulus MA of the mitral valve cavity. Once the arm members of the retractor device are at a desired separation relationship, the respective positioning of the arm members can be locked using a locking mechanism, such as by a screw and lock nut arrangement, or the like.

In accordance with an aspect of the present invention, the longitudinal projection on the anterior side of the retractor device is longer than the corresponding longitudinal projection on the posterior side to accommodate the longer size of the anterior leaflet in comparison with the posterior leaflet and project deeper into the mitral valve cavity. Correspondingly, the longitudinal projection on the posterior side is shorter/smaller to accommodate the shorter posterior leaflet. In general, the retractor device, when in use, has essentially a semicircular shape, as the focus in mitral valve surgeries is typically only on one side of the mitral valve apparatus at a time. In this regard, the retractor device can have distinct "left" and "right" forms—that is, a "left form" for positioning the retractor device on the left side of the mitral valve—as associated with the anterior lateral papillary muscle designated in FIG. 1B—and a "right form" for positioning the retractor device on the right side of the mitral valve—as associated with the posterior medial papillary muscle designated in FIG. 1B.

Accordingly, separate "left" and "right" retractor devices are envisioned in accordance with the present invention and can be used, as needed, depending on which papillary muscle PM is in need of repair. For example, separate retractor devices can be provided for the anterolateral and posteromedial papillary muscles. These "left" and "right" retractor devices are preferably mirror images of one another. The present invention further allows for multiple retractor devices to be used together without inhibiting the operative procedure. Thus, while it is generally understood that one retractor device is generally only needed for each procedure, two opposing retractor devices of identical but mirror configurations can be used at the same time, in accordance with the spirit and principles of the present invention, if a procedure requires work on the entire mitral valve apparatus without interfering with each other. The ease of adjustment of the retractor device described herein also makes it easy to manually position and adjust such devices relative to not only the surrounding muscle and tissue, but also to one another.

In an aspect of the present invention, the retractor device does not include any spring bias. Instead, the arm members can be manually opened and closed as desired, giving the surgeon full control of the retractor device. Once a desired position and angular spread is selected, the arm members can be locked relative to each other, such as by a setscrew, or a lock screw and locknut combination, or the like. In alternate embodiments, a spring mechanism can be provided in the retractor device without affecting the principles and spirit of the present invention.

Additional features can be provided, for example, suction means can be incorporated into the retractor device to suck collected blood from the surrounding cavity for better exposure. For example, suction holes can be provided in each or either of the longitudinal projections. Such holes can be connected with a suction feed to draw out blood from the mitral valve cavity.

Additionally, a long handle can be attached to the retractor device to aid in insertion and removal of the retractor device from the mitral valve opening MA during minimal invasive surgery when working in a deeper cavity, as well as to aid in opening and closing the arm members relative to one another, especially once the retractor device has been located at a desirable working position. Such a handle can also aid use of a suction means, as described above. For example, suction feed tubes can be run along or even within such a handle and connected to a vacuum means.

In another embodiment, lights may be provided on the ends of the longitudinal projections and/or along the arm members at the rim MA of the mitral valve cavity to increase visibility within the mitral valve cavity.

These and other objects, features and advantages of the present invention will become apparent in light of the detailed description of embodiments thereof, as illustrated in the accompanying drawings.

BRIEF DESCRIPTION OF THE DRAWINGS

FIGS. 3A and 3B illustrate top planar views of an embodiment of a hands-free mitral papillary muscle retractor device in accordance with the present invention. In FIG. 3A, the retractor device is closed to a non-use condition whereby the retractor device can be inserted into the mitral valve cavity for use. FIG. 3B shows the retractor device opened to a condition representative of when such a retractor device is being used once in a desired position relative to the mitral valve cavity of the patient.

DETAILED DESCRIPTION OF PREFERRED EMBODIMENTS

Embodiments of a hands-free mitral papillary muscle retractor device in accordance with the present invention is illustrated in FIGS. 2-12 and generally designated by reference numeral 100. FIG. 2 provides an intraoperative image of mitral valve exposure illustrating the depth of the mitral valve in an operative setting and thus providing some context for use of the retractor device 100 of the present invention.

As noted above, with reference to the schematic illustration of a mitral valve apparatus provided in FIG. 1B, the "mitral valve apparatus" generally constitutes the anterior lateral and posterior medial papillary muscles PM, which arise from the heart muscle, the anterior and posterior mitral leaflets AL and PL, and chordae tendineae CT, which are attached to the two papillary muscles PM. The mitral valve MV consists of two leaflets—the anterior leaflet AL and the posterior leaflet PL—which open during relaxation of the heart and close when the heart contracts while pushing blood into the body. The chordae tendineae CT are attached between the papillary muscles PM and the leaflets AL, PL to prevent blood from returning into the atrium via the mitral valve MV. Mitral valve repair is commonly needed to repair elongated or torn chordae tendineae CT. In use, the retractor device is generally placed at the opening or rim (i.e., the mitral annulus MA) of the mitral valve cavity to hold back the leaflets AL, PL and tissue and to provide access to the mitral valve cavity and papillary muscles.

Figure 3A:
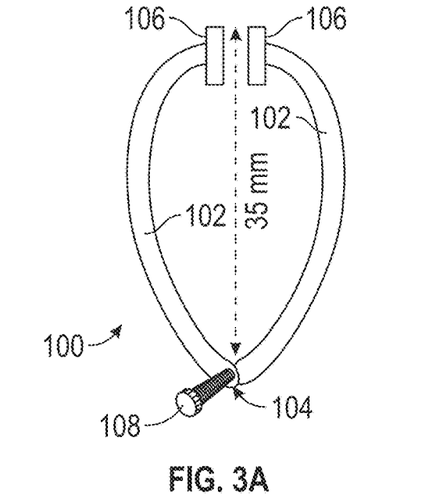
Figure 3B:
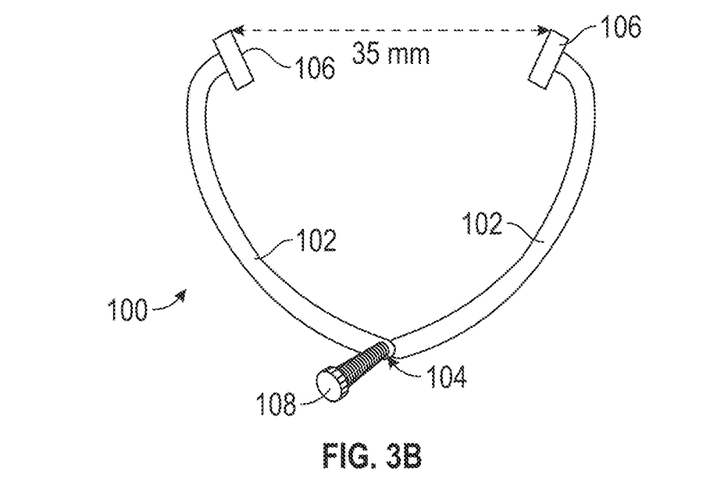

Referring to the embodiment of the retractor device 100 illustrated in FIGS. 3A and 3B, a pair of arm members 102 are pivotally connected to one another and can be manually spread apart and adjusted about a pivot point 104 to a desired angular arrangement to one another, and placed in position relative to the mitral valve apparatus to prevent injury to surrounding muscle and tissue during an operative procedure. Each arm member 102 includes a respective downwardly/outwardly extending longitudinal projection 106 to hold one of the anterior and posterior leaflets adjacent to said arm member 102 when the retractor device 100 is positioned relative to the mitral valve apparatus.

Figure 5:
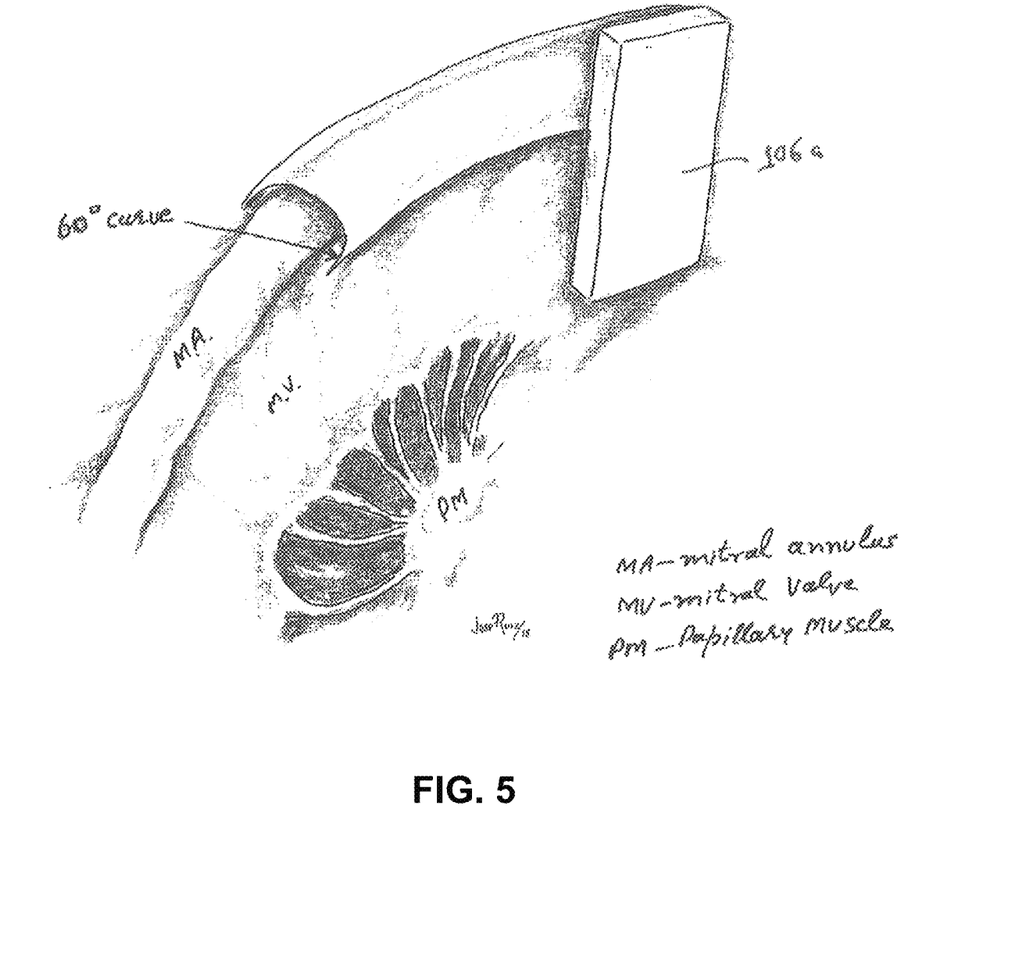
FIG. 5 illustrates an anterior longitudinal projection of the retractor device of FIGS. 3A-3B in a preferred position relative to the mitral annulus, mitral valve and papillary muscle of a patient.

In FIG. 3A, the retractor device 100 is closed to a non-use condition whereby the retractor device 100 can be inserted into the mitral valve cavity for use. FIG. 3B shows the retractor device 100 opened to a condition representative of when such a retractor device 100 is being used once in a desired position relative to the mitral valve cavity of the patient. FIG. 5 partially illustrates the retractor device 100 in position relative to the mitral valve cavity, with an anterior longitudinal projection 106a positioned relative to the mitral annulus MA, or rim, of the mitral valve cavity, and hold back the leaflet and chordae tendineae of the mitral valve MV. The arm members 102 are preferably curved, as illustrated, to generally correspond to the shape of the mitral valve cavity and the mitral annulus MA. Thus, the present invention provides a hands-free mitral papillary muscle retractor device 100 that provides a clear view of the pathology of the leaflets AL, PL and chordae tendineae CT of a mitral valve apparatus, while also providing a clear view of the entire papillary muscle PM needing repair.

In accordance with an aspect of the present invention, the arm members 102 of the retractor device 100 can be manually opened and closed as desired, giving the surgeon full control of the retractor device 100. Once a desired position and spread is selected, the arm members 102 can be locked relative to each other using a locking mechanism, illustrated in FIGS. 3A and 3B as a setscrew 108. The surgeon can simply tighten the screw 108 once a desired relative arrangement of the arm members 102 is achieved. The screw 108 can be loosened to permit adjustment of the arm members 102 relative to one another, or to close the arm members 102 so that the retractor device 100 can be removed from the mitral valve cavity. In alternate embodiments of the present invention, the arm members 102 may be spring biased to a "closed" condition, if desired.

Figure 4A:
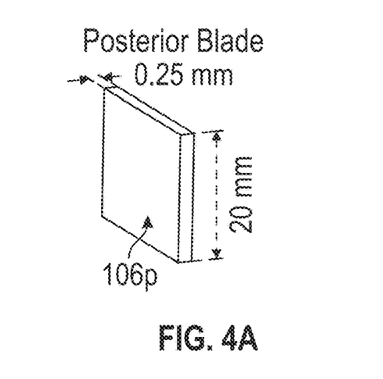
FIGS. 4A and 4B illustrate, respectively, an embodiment of a posterior longitudinal projection and an anterior longitudinal projection for use on the retractor device of FIGS. 3A-3B.
Figure 4B:
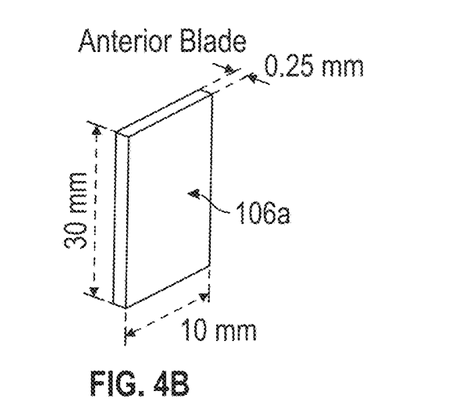

When the retractor device 100 is positioned relative to the mitral valve cavity, the longitudinal projections 106 are aligned and positioned relative to the anterior and posterior leaflets AL, PL so as to be able to push said leaflets open and hold them during mitral repair surgery. Referring to FIGS.

4A and 4B, the longitudinal projection 106a on the anterior side of the retractor device 100 is longer than the corresponding longitudinal projection 106p on the posterior side to accommodate the longer size of the anterior leaflet AL in comparison with the posterior leaflet PL and project deeper into the mitral valve cavity. Correspondingly, the longitudinal projection 106p on the posterior side is shorter/smaller to accommodate the shorter posterior leaflet PL. Representative dimensions are presented in FIGS. 4A-4B, but such dimensions can vary without departing from the spirit and principles of the present invention.

In general, the retractor device 100, when in use, has essentially a semicircular shape, as generally illustrated in FIG. 3B, as the focus in mitral valve surgeries is typically only on one side of the mitral valve apparatus at a time. In this regard, the retractor device 100 can have distinct "left" and "right" forms—that is a "left form" for positioning the retractor device 100 on the left side of the mitral valve MV—as associated with the anterior lateral papillary muscle designated in FIG. 1B—and a "right form" for positioning the retractor device 100 on the right side of the mitral valve MV—as associated with the posterior medial papillary muscle designated in FIG. 1B.

Accordingly, separate "left" and "right" retractor devices 100 are envisioned in accordance with the present invention. These "left" and "right" retractor devices 100 are preferably mirror images of one another. While it is generally understood that one retractor device is needed for each procedure, two opposing retractor devices of identical but mirror configurations can be used at the same time, in accordance with the spirit and principles of the present invention, if a procedure requires work on the entire mitral valve apparatus. Moreover, the design of the retractor device 100 presented herein permits two such devices 100 to be used at the same time without interfering with each other or the surgical procedure.

A "right" retractor device 100 in accordance with the present invention is illustrated in FIGS. 6-12. As illustrated, the anterior longitudinal projection 106a is longer than the posterior longitudinal projection 106p. Each projection 106 extends downwardly at the end of a respective curved arm member 102. The arm members 102 are pivotally connected at a pivot point 104 that further includes a locking mechanism 108 generally comprising a thumbscrew 110 received in a locking hex nut 112, as shown in the exploded view of FIG. 12. The thumbscrew 110 extends upwardly from the top of the arm members 102, provided easy access to a surgeon, while the hex nut 112 is seated within a cap 114 that restricts movement of the hex nut 112 to facilitate locking of the relative position of the arm members 102 when the thumbscrew 110 is tightened. Similarly, when the thumbscrew 110 is loosened, the relative position of the arm members 102 can be adjusted.

Figure 6:
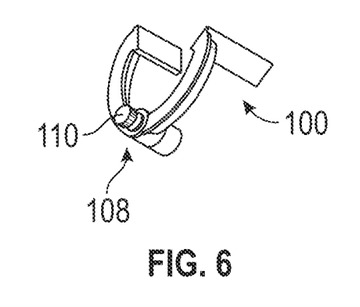
FIG. 6 illustrates a perspective view of another embodiment of a hands-free mitral papillary muscle retractor device in accordance with the present invention.
Figure 7:
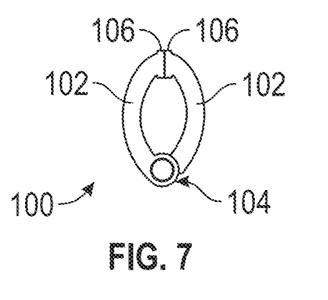
FIG. 7 illustrates a top planar view of the retractor device of FIG. 6 in a closed condition for insertion into a patient.
Figure 8:
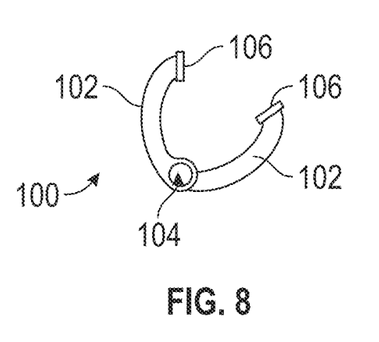
FIG. 8 illustrates a top planar view of the retractor device of FIG. 6 in an opened condition representative of when such a device is being used once in a desired position in the patient.
Figure 11:
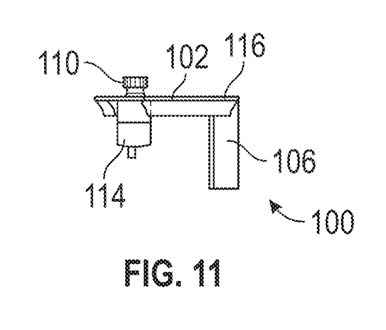
FIG. 11 illustrates another planar right-hand side view of the retractor device of FIG. 6 when the arms are closed relative to one another.
Figure 12:
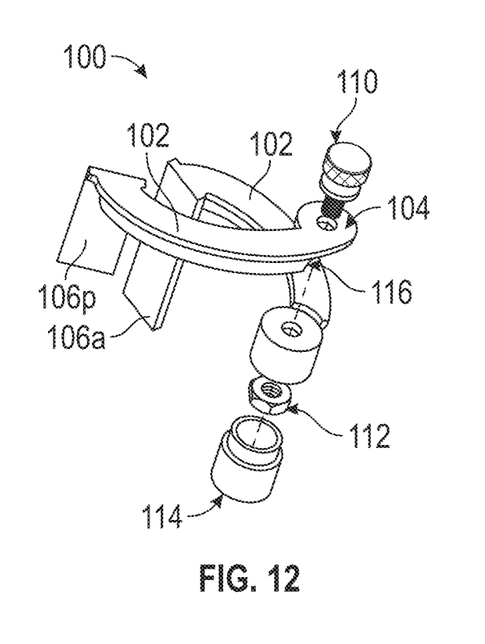
FIG. 12 illustrates an exploded perspective view of the retractor device of FIG. 6.

A "closed" condition of the arm members 102 is illustrated in FIGS. 7 and 11. An "open" or "use" condition of the arm members 102 is illustrated in FIGS. 6 and 8-10.

Figure 9:
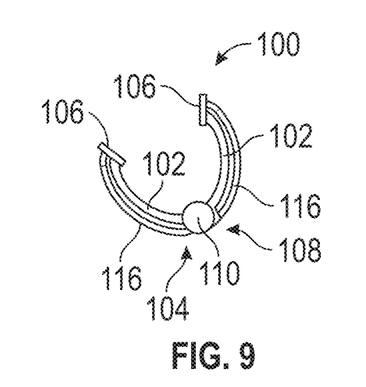
FIG. 9 illustrates a bottom planar view of the retractor device of FIG. 6 in the opened condition.
Figure 10:
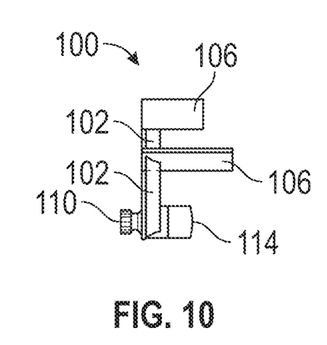
FIG. 10 illustrates a planar right-hand side view of the retractor device of FIG. 6.

As illustrated in FIGS. 6 and 9, each arm member 102 has a generally arcuate shape so that the arm members 102 do not interfere with access to the mitral valve cavity when properly positioned. Further, each of the arm members 102 includes a ridge 116 extending in a plane that is generally normal to the downwardly extending longitudinal projections 106. These ridges 116 are adapted to be seated at the opening MA of the mitral valve cavity during use of the retractor device 100.

Figure 13:
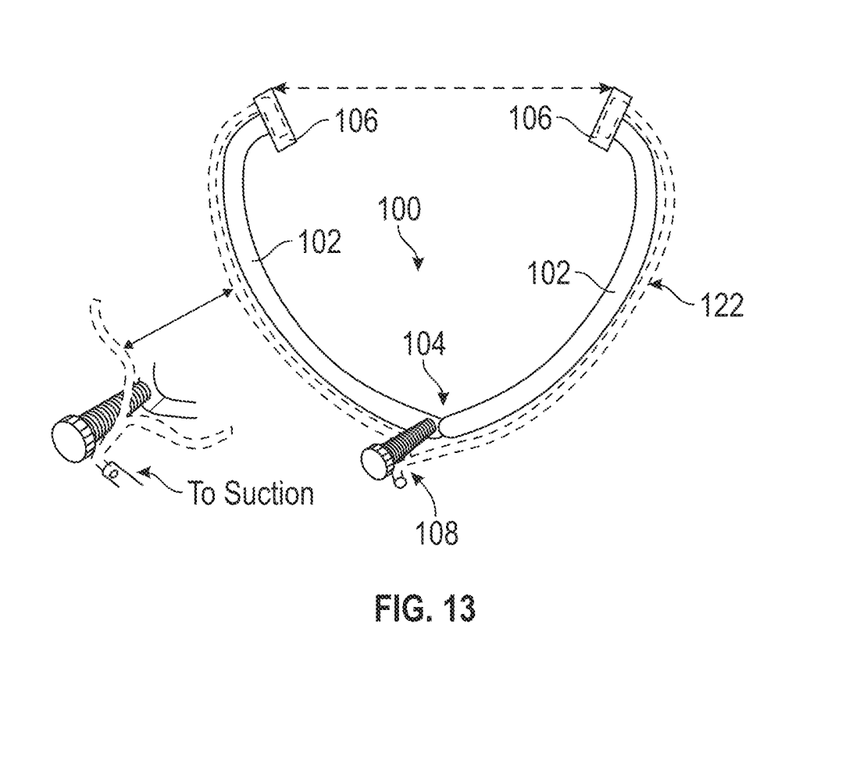
FIG. 13 illustrates a top planar view of another embodiment of a hands-free mitral papillary muscle retractor device in accordance with the present invention incorporating a suction means.
Figure 14:
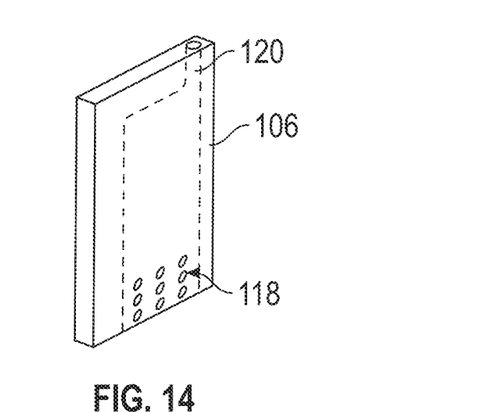
FIG. 14 illustrates another embodiment of a longitudinal projection for use on the retractor device of FIG. 13.

Additional features can be provided without affecting the principles and spirit of the present invention. For example, suction means can be incorporated into the retractor device to suck collected blood from the surrounding mitral valve cavity for better exposure. For example, as illustrated in FIG. 14, suction holes 118 can be provided in one or both of the longitudinal projections 106. As illustrated, the suction holes 118 are provided at the lower end of the projection 106 and are connected via a cavity 120 to a suction feed or tubes 122 running along or within the arm members 102 to draw out blood from the mitral valve cavity. The suction feed 122 can lead out of the mitral valve cavity proximate to the pivot point 104 of the retractor device 100, as illustrated in FIG. 13.

Figure 15:
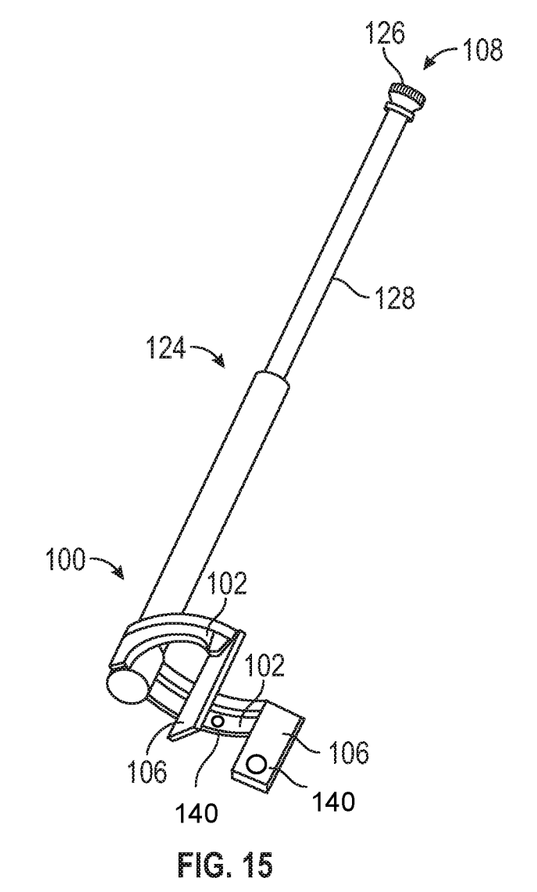
FIG. 15 illustrates a perspective view of another embodiment of a hands-free mitral papillary muscle retractor device in accordance with the present invention incorporating a handle.
Figure 16:
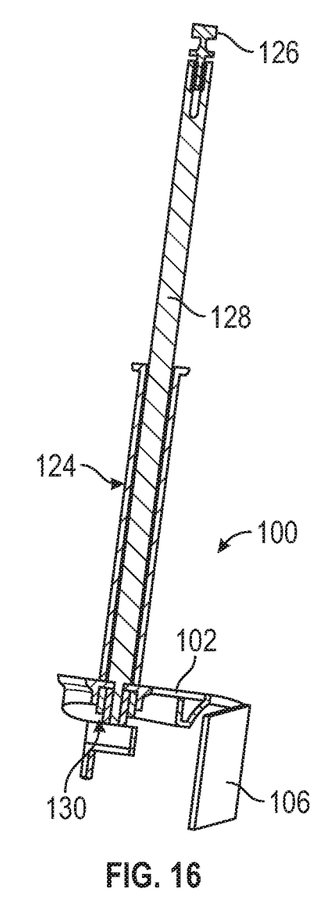
FIG. 16 illustrates a cross-sectional view of the retractor device of FIG. 15.

Additionally, a handle 124 can be attached to the retractor device 100, as illustrated in FIGS. 15-16, to aid in insertion and removal of the retractor device 100 from the mitral valve opening MA during minimal invasive surgery when working in a deeper cavity, as well as to aid in opening and closing the arm members 102 relative to one another, especially once the retractor device 100 has been located at a desirable working position. As illustrated, the handle 124 projects in an opposite direction from the downwardly/outwardly extending longitudinal projections 106. The locking mechanism 108 may be positioned at an upward end of the handle 124 for locking the position of the arm members 102 relative to one another. As illustrated, the locking mechanism 108 comprises a thumbscrew 126 that turns a handle shaft 128 and engages a locking nut 130 seated within the retractor device 100. The locking mechanism 108 can further be used to manipulate the relative positioning of the arm members 102 prior to locking said arm members 102 in place. In this regard, rotation of the handle shaft 128 can effect movement of the arm members 102 about the pivot point 104 until a set or desired position is reached. The handle 124 can be either pushed or pulled to engage the locking nut 130 to then be able to lock the arm members 102 in place. Further, a torsion spring or the like can be provided at the base of the handle 124 to aid in positioning the arm members 102 relative to one another. Such a handle 124 can also aid use of a suction means, as described above. For example, suction feed tubes can be run along or even within such a handle 124 and connected to a vacuum means.

In another embodiment of the present invention, lights 140 may be provided on the ends of the longitudinal projections 106 and/or along the arm members 102 at the rim (mitral annulus MA) of the mitral valve cavity, as illustrated in FIG. 15, to increase visibility within the mitral valve cavity.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A mitral papillary muscle exposure device for positioning relative to and into a cavity of a mitral valve apparatus during surgery on said mitral valve apparatus to facilitate access thereto, said cavity having an annulus extending along an annulus plane through which the mitral papillary muscle exposure device extends when positioned for surgery, said device comprising:
   a first member and a second member, each having a proximal end and a distal end, wherein said first member and said second member are connected to one another at the respective proximal ends and pivotably moveable relative to one another; and a locking mechanism for locking a position of the first member relative to the second member, wherein each of the first member and the second member comprises a respective first portion generally extending in a first planar direction and a second portion positioned at the distal end of said first or second member generally extending in a second planar direction different from the first planar direction, wherein the first portion of each of the first and second members is adapted for placement along the annulus and, when so placed, the first planar direction thereof is generally parallel to the annulus plane and the second portion projects into the cavity of the mitral valve apparatus.

2. The mitral papillary muscle exposure device according to claim 1, wherein the second portion of the first member is longer than the second portion of the second member.

3. The mitral papillary muscle exposure device according to claim 1, wherein the second portion of each of the first and second members includes suction openings connected with suction tubes feeding out of the device.

4. The mitral papillary muscle exposure device according to claim 1, further comprising lights provided on the device for illuminating the mitral valve apparatus.

5. The mitral papillary muscle exposure device according to claim 4, wherein the lights are positioned on the second portion of each of the first and second members.

6. The mitral papillary muscle exposure device according to claim 1, wherein the first and second members are pivotally connected to one another for movement to a position where said first and second members have an essentially angular relationship to one another at a pivot point.

7. The mitral papillary muscle exposure device according to claim 1, wherein the first and second members are curved so as to resemble an annulus of the cavity of the mitral valve apparatus when the first and second members are pivotably moved relative to one another.

8. The mitral papillary muscle exposure device according to claim 1, wherein the locking mechanism comprises a screw and locking nut.

9. The mitral papillary muscle exposure device according to claim 1, further comprising a handle projecting in an opposite direction from the second portions to aid in insertion and removal of the device relative to the cavity of the mitral valve apparatus.

10. The mitral papillary muscle exposure device according to claim 9, wherein the locking mechanism is positioned at an upward end of the handle and can further be used to manipulate the relative position of the first member and second member prior to locking said members in place.

11. The mitral papillary muscle exposure device according to claim 9, further comprising suction openings provided on the second portion of each of the first and second members connected with suction tubes feeding out of the retractor, wherein said suction tubes are fed through the handle.

12. A mitral papillary muscle exposure device for positioning relative to a cavity of a mitral valve apparatus during surgery on said mitral valve apparatus, said device comprising:

a first member having a downwardly extending longitudinal projection;

a second member having a downwardly extending longitudinal projection;

wherein said first member and said second member are pivotably moveable relative to one another; and a locking mechanism for locking a position of the first member relative to the second member, wherein the first and second members are curved so as to resemble an opening of the mitral valve cavity when the first and second members are pivotably moved relative to one another, wherein each of the first and second members includes a ridge in a plane that is generally normal to the longitudinal projections of each of the first and second members, wherein said ridges on said first and second members are adapted to be seated at the opening of the cavity of the mitral valve apparatus during use of the device.

13. A mitral papillary muscle exposure device positioning relative to and into a cavity of a mitral valve apparatus during surgery on said mitral valve apparatus to facilitate access thereto, said cavity having an annulus extending along an annulus plane through which the mitral papillary muscle exposure device extends when positioned for surgery, said device comprising:

a curved anterior member having a proximal end and a distal end; and a curved posterior member having a proximal end and a distal end;

wherein said anterior member and said posterior member are pivotably connected to one another at respective proximal ends thereof for movement relative to one another about a pivot point, wherein each of the anterior member and the posterior member comprises a respective first curved portion generally extending in a first planar direction and a second portion positioned at the distal end of said anterior or posterior member generally extending in a second planar direction different from the first planar direction, wherein the first curved portion of each of the anterior and posterior members is adapted for placement along the annulus and, when so placed, the first planar direction thereof is generally parallel to the annulus plane and the second portion projects into the cavity of the mitral valve apparatus.

14. The mitral papillary muscle exposure device according to claim 13, further comprising a locking mechanism for locking a position of the anterior member relative to the posterior member.

15. The mitral papillary muscle exposure device according to claim 14, wherein the locking mechanism comprises a screw and locking nut.

16. The mitral papillary muscle exposure device according to claim 13, wherein the second portion of the anterior member is longer than the second portion of the posterior member.

17. The mitral papillary muscle exposure device according to claim 13, wherein the second portion of at least one of the anterior and posterior members includes suction openings connected with suction tubes feeding out the device.

18. The mitral papillary muscle exposure device according to claim 13, further comprising lights provided on the device for illuminating the mitral valve apparatus.

19. The mitral papillary muscle exposure device according to claim 18, wherein the lights are positioned on the second portion of at least one of the anterior and posterior members.

20. The mitral papillary muscle exposure device according to claim 13, wherein the curvature of the anterior and posterior members resembles an annulus of the cavity of the mitral valve apparatus when the anterior and posterior members are pivotably moved relative to one another.

21. The mitral papillary muscle exposure device according to claim 13, further comprising a handle projecting in an opposite direction from the second portions to aid in insertion and removal of the device relative to the cavity of the mitral valve apparatus.

22. The mitral papillary muscle exposure device according to claim 21, further comprising a locking mechanism for locking a position of the anterior member relative to the posterior member that is positioned at an upward end of the handle.

23. The mitral papillary muscle exposure device according to claim 22, wherein the locking mechanism can be used to manipulate the relative position of the anterior member and the posterior member prior to locking said members in place.

24. The mitral papillary muscle exposure device according to claim 22, wherein the locking mechanism comprises a screw and locking nut.

25. The mitral papillary muscle exposure device according to claim 21, further comprising suction openings provided on the second portions of each of the anterior and posterior members connected with suction tubes feeding out of the device,
wherein said suction tubes are fed through the handle.

26. A mitral papillary muscle exposure device for positioning relative to a cavity of a mitral valve apparatus during surgery on said mitral valve apparatus, said device comprising:
a curved anterior member having a downwardly extending longitudinal projection at a first end thereof; and
a curved posterior member having a downwardly extending longitudinal projection at a first end thereof;
wherein said anterior member and said posterior member are pivotably connected to one another at respective second ends thereof for movement relative to one another about a pivot point,
wherein the curvature of the anterior and posterior members resembles an opening of the mitral valve cavity when the anterior and posterior members are pivotably moved relative to one another,
wherein each of the anterior and posterior members includes a ridge in a plane that is generally normal to the longitudinal projections of each of said members, wherein said ridges on said anterior and posterior members are adapted to be seated at the opening of the cavity of the mitral valve apparatus during use of the device and hold respective anterior and posterior leaflets of the mitral valve apparatus.

* * * * *